United States Patent
Tsukamoto et al.

(10) Patent No.: US 12,194,114 B2
(45) Date of Patent: Jan. 14, 2025

(54) DENTAL GLASS IONOMER CEMENT COMPOSITION SUITABLE FOR MECHANICAL MIXING

(71) Applicant: KABUSHIKI KAISHA SHOFU, Kyoto (JP)

(72) Inventors: Masahiro Tsukamoto, Kyoto (JP); Shuji Sakamoto, Kyoto (JP); Katsuya Kimoto, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 208 days.

(21) Appl. No.: 17/520,098

(22) Filed: Nov. 5, 2021

(65) Prior Publication Data

US 2022/0142875 A1   May 12, 2022

(30) Foreign Application Priority Data

Nov. 10, 2020 (JP) ................................. 2020-186987
Nov. 2, 2021 (JP) ................................. 2021-179701

(51) Int. Cl.
*A61K 6/20* (2020.01)
*A61K 6/60* (2020.01)
*A61K 6/889* (2020.01)

(52) U.S. Cl.
CPC ................ *A61K 6/889* (2020.01); *A61K 6/20* (2020.01); *A61K 6/60* (2020.01)

(58) Field of Classification Search
CPC ...................................................... A61K 6/889
See application file for complete search history.

(56) References Cited

U.S. PATENT DOCUMENTS 5,051,453 A    9/1991    Okabayashi et al.

FOREIGN PATENT DOCUMENTS

| EP | 0 588 950 | 3/1994 |
|----|-----------|--------|
| JP | 1-308853 | 12/1989 |
| WO | 92/21632 | 12/1992 |
| WO | 2015/088956 | 6/2015 |

OTHER PUBLICATIONS

Extended European Search Report issued Mar. 25, 2022 in European Patent Application No. 21207066.8.

*Primary Examiner* — Benjamin J Packard
(74) *Attorney, Agent, or Firm* — Wenderoth, Lind & Ponack, L.L.P.

(57) ABSTRACT

The present invention provides a dental glass ionomer cement composition which can improve the mixing efficiency of a powder and a liquid to an extent where their powder to liquid ratio can be raised in mechanical mixing without reducing a fluoride-release property, and further expresses a high mechanical property. More specifically, the present invention provides a dental glass ionomer cement composition in which a powder and a liquid are separately packaged in a dental capsule, and the powder and the liquid are used by mixing immediately before their use, wherein the composition comprises (a) a hydrophobized acid reactive glass powder, (b) a polyalkene acid, and (c) water, and is not accompanied by a polymerization reaction upon setting.

6 Claims, No Drawings

DENTAL GLASS IONOMER CEMENT COMPOSITION SUITABLE FOR MECHANICAL MIXING

TECHNICAL FIELD

The present invention relates to a dental glass ionomer cement composition which is not accompanied by a polymerization reaction upon curing and mainly set under an acid-base reaction, and is used as a glass ionomer cement for a dental filling, a glass ionomer cement for dental luting, etc.

BACKGROUND ART

In a dental clinical practice, in order to carry out an aesthetic and functional recovery for teeth whose shape was partially spoiled by dental caries, fracture, etc., a direct restoration to fill teeth with a filling material and an indirect restoration to lute and/or adhere a dental prosthesis equipment to teeth by using a luting material have been carried out. Examples of representatives of the filling material or luting material include a dental glass ionomer cement to be cured with only an acid-base reaction, or a resin modified glass ionomer cement to be cured by being also accompanied by a polymerization reaction in addition to an acid-base reaction. In the case of focusing on strengthening the teeth or inhibition of a secondary dental caries, a dental glass ionomer cement having a higher fluoride-release property is suitable.

The dental glass ionomer cement is generally provided in a form divided into a powder which has an acid reactive glass powder as main components, and a liquid which has a polyalkene acid and water as main components, and the powder and the liquid are used by mixing immediately before their use, As the mixing method of the dental glass ionomer cement, there are a hand mixing in which the powder and liquid measured in quantity by a specified method was taken out on a mixing paper from a container, in which the powder and the liquid are packaged to knead them using an instrument such as a spatula; and a mechanical mixing in which a previous quantity measured powder and liquid in a state such that they are isolated in a dental capsule designed as a single use, are contacted with each other in the dental capsule by a specified method, and then they are mixed by adding a quick and strong vibration in a capsule mixer.

REFERENCE DOCUMENTS

Patent Documents

Patent Document 1: JP-A No. 01-308853

SUMMARY OF THE INVENTION

Problems to be Solved by the Invention

When the powder and liquid are mixed, an acid-base reaction between the acid reactive glass powder and the polyalkene acid under the presence of water will advance to set the dental glass ionomer cement. And, the mechanical property of a setting material of the dental glass ionomer cement is improved as the rate of the acid reactive glass powder contained in all components generally becomes higher. For this reason, it is preferable that the mass ratio of the powder to the liquid, namely, powder to liquid ratio is as higher as possible. However, as the powder to liquid ratio becomes higher, the viscosity of cement mixture becomes higher. Therefore, if the powder to liquid ratio is too much higher, it may not be fully mixed, and may become an uneven cement mixture, and thereby the reduction of the mechanical property of their setting material may occur on the contrary. For this reason, there is a certain limitation to make the powder to liquid ratio higher.

A dental glass ionomer cement composition has been proposed so far whose powder to liquid ratio can be higher, and thereby in which a resulting setting material expresses high mechanical property. For example, Patent Document 1 discloses a technology to make a powder to liquid ratio higher by containing spherical coarse inorganic oxide particles having a large particle size, and fine inorganic oxide particles having a small particle size at a specific rate in a dental glass ionomer cement composition.

When a powder and a liquid of a dental glass ionomer cement are hand mixed using a spatula etc., strong shearing force and compressive force can be applied to their cement mixture. On one hand, when the powder and the liquid are mechanically mixed within the dental capsule, the powder and the liquid are mixed by adding a fine and strong vibration to the dental capsule in a capsule mixer by the dental capsule. However, it is generally difficult to add a strong force to their cement mixture, as compared with the hand mixing. Therefore, it has been difficult to increase the powder to liquid ratio as compared with the hand mixing.

Furthermore, for the dental glass ionomer cement composition of Patent Document 1, there is needed to separately manufacture the spherical coarse inorganic oxide particle and the fine inorganic oxide particles, and further for the spherical coarse inorganic oxide particles, since the inorganic oxide particles are melted in a dispersion state to manufacture them by spheroidizing the particles with a surface tension, the manufacturing steps are complicated and further control of their particle size was difficult. Furthermore, since fluoride is seceded from the inorganic oxide particle in a step for melting and spheroidizing them, the fluoride-release property which is one of the large features of the dental glass ionomer cement might have been reduced.

Therefore, the object of the present invention is to provide a dental glass ionomer cement composition which can improve mixing efficiency of the powder and the liquid to an extent where the powder to liquid ratio can be raised in a mechanical mixing without reducing a fluoride-release property, and further which expresses a high mechanical property.

Means for Solving the Problems

The present inventors found out unexpectedly that in a dental glass ionomer cement composition which comprises an acid reactive glass powder, a polyalkene acid and water and is not accompanied by a polymerization reaction upon curing, the mixing efficiency of a powder and a liquid is improved even to such an extent where powder to liquid ratio can be raised in a mechanical mixing, without reducing a fluoride-release property by appropriately hydrophobizing the surface of the acid reactive glass powder moderately with a hydrophobizing surface treatment agent, and thereby that its mechanical property is improved. And the present invention was completed.

Namely, the present inventors found out that the aforementioned problems can be solved by the following constitutions:

The present invention is a dental glass ionomer cement composition to be mechanically mixed by using a mixing equipment or device for capsulation, comprising: (a) a hydrophobized acid reactive glass powder, (b) a polyalkene acid, and (c) water, wherein the dental glass ionomer cement composition is not accompanied by a polymerization reaction upon curing, in other words, the dental glass ionomer cement composition does not undergo a polymerization (polymerization process) upon curing.

Effects of the Invention

In the dental glass ionomer cement composition of the present invention, a powder and a liquid are efficiently mixed by their mechanical mixing. Further, since the powder to liquid ratio can be thereby set to a higher ratio, a desired high mechanical property can be expressed. Furthermore, since the dental glass ionomer cement composition has a desired high fluoride-release property, it is effective for strengthening the teeth or an inhibition of the secondary caries.

MODES FOR CARRYING OUT THE INVENTION

Hereinafter, the present invention is explained in detail.

In the present description, the "dental glass ionomer cement" means a powder-liquid type dental glass ionomer cement in which a compound having a polymerizable groups, such as a polymerizable monomer, an oligomer having polymerizable group(s) and/or a polymer having polymerizable group(s), is not blended by intending that the compound confers curing by a polymerization reaction; and which is set mainly by an acid-base reaction which occurs between an acid reactive glass powder and a polyalkene acid under the presence of water.

The "dental capsule" means a capsule to be used in mixing equipments for capsulation, and/or capsule for mixing and dispensing dental materials.

And, the "mechanical mixing" means that a powder and a liquid which have been prepackaged in an isolated state within the dental capsule, or a powder and a liquid which are filled into the dental capsule immediately before their use, are mixed by adding a fine and strong vibration to the dental capsule in a capsule mixer.

Further, the "capsule mixer" is an equipment or device capable of mounting the dental capsule(s), and is the equipment or device for mixing the powder and the liquid by adding a fine and strong vibration to the dental capsule(s). Furthermore, the "hydrophobizing surface treatment agent" means a compound which can surface treat the acid reactive glass powder, and can modify the surface of the acid reactive glass powder to a hydrophobicity by surface treating using it.

The dental glass ionomer cement composition of the present invention comprises (a) a hydrophobized acid reactive glass powder, (b) a polyalkene acid, and (c) water as essential components, and the mixing efficiency of the powder and the liquid is improved in a mechanical mixing by this component composition.

Therefore, the dental glass ionomer cement composition of Patent Document 1 essentially and completely differs from the dental glass ionomer cement composition of the present invention in that the former contains the spherical coarse inorganic oxide particles having a large particle size, whereas the latter does not contain them.

Hereinafter, the aforementioned components of the present invention are explained.

The hydrophobized acid reactive glass powder (a) which can be used for the dental glass ionomer cement composition of the present invention, is an acid reactive glass powder which is appropriately hydrophobed on its surface by surface treating the acid reactive glass powder to be generally used to the dental glass ionomer cement composition by using a known hydrophobizing surface treatment agent. By using the hydrophobized acid reactive glass powder (a) for the dental glass ionomer cement composition, the mixing efficiency of the powder and the liquid is improved even to an extent where the powder to liquid ratio can be raised in mechanical mixing without reducing a fluoride-release property, and thereby its mechanical property is improved. The fluoride-release property is preferably a high fluoride-release property which is the same level as that of existing dental glass ionomer cements. In addition, in only the mechanical mixing, the mixing efficiency of the powder and the liquid is improved by hydrophobizing the acid reactive glass powder, whereas in the hand mixing, the mixing efficiency is not changed, or worsens on the contrary.

The acid reactive glass powder which can be used upon producing the hydrophobized acid reactive glass powder (a) needs to contain an acid reactive element such as a metallic element, and a fluorine element. When the acid reactive glass powder contains the acid reactive element, an acid-base reaction with an acidic group which the polyalkene acid (b) has, advances under the presence of the water (c). By specifically illustrating the acid reactive element, its examples include, but not limited to, sodium, potassium, calcium, strontium, barium, lanthanum, aluminium, and zinc. These acid reactive elements can be included in one kind or two kinds or more, and their contents are not particularly limited.

Furthermore, in order to confer an X-ray imaging property to the dental glass ionomer cement composition of the present invention, the acid reactive glass powder preferably contains X-ray radiopaque element(s). By specifically illustrating the X-ray radiopaque element(s), their examples include, but not limited to, strontium, lanthanum, zirconium, titanium, yttrium, ytterbium, tantalum, tin, tellurium, tungsten, and bismuth. Furthermore, for the other elements which are contained in the acid reactive glass powder, there is particularly no limitation, and the acid reactive glass powder in the present invention can contain various elements.

As the acid reactive glass powder, aluminosilicate glass, borosilicate glass, aluminoborate glass, boroaluminosilicate glass, phosphate glass, boric acid glass, and silica glass, etc., which contain the aforementioned acid reactive element, fluorine, and X-ray radiopaque element(s) are illustrated, and but it is not limited thereto.

Furthermore, the particle shape of the acid reactive glass powder is not particularly limited, and the acid reactive glass powder having an arbitrary particle shape, such as a globular, needle, tabular, granular, or scale shape, can be used without any restrictions. These acid reactive glass powders can be used alone or in a combination of a few kinds.

The production method of these acid reactive glass powders is not particularly limited, and any production methods, such as a scorification method, a gaseous phase method, and a sol-gel method can be used without any problems. Among them, the acid reactive glass powder produced by the scorification or sol-gel method which is easy to control the kind or content of elements, is preferably used.

The acid reactive glass powder can be pulverized and used to have a desired particle size. The pulverizing method is not particularly limited, and the acid reactive glass powder which was pulverized using any pulverizing methods of a wet method or dry process can be used. Specifically, the desired particle size can be adjusted by pulverizing the acid reactive glass powder using a high speed revolution mill such as a hammer mill and a turbo mill, a ball mill, a container driving type mill such as a planetary mill and a vibration mill, a medium stirrer mill such as an attritor and a bead mill, a jet mill, etc., depending on use or use purpose of the dental glass ionomer cement composition of the present invention.

The hydrophobized acid reactive glass powder (a) of the dental glass ionomer cement composition may be one obtainable by hydrophobization-treating an acid reactive glass powder having 50% particle size (D50) in an accumulation particle size distribution on a volume basis of 0.5 to 15 μm with the hydrophobizing surface treatment agent. In such the case, the mixing efficiency and/or mechanical property are easy to be improved.

Thus, the 50% particle size (D50) of the acid reactive glass powder suitable for the dental glass ionomer cement composition of the present invention, is preferably in a range from 0.5 to 15 μm. The "50% particle size (D50)" means a particle size when the cumulative value from the small particle size side becomes 50%, in a particle size distribution on a volume basis measured using a laser diffraction-dispersion particle size distribution measuring apparatus, etc.

Furthermore, when the dental glass ionomer cement composition of the present invention is used as a material for filling, the 50% particle size (D50) of the acid reactive glass powder is preferably in a range from 3 to 15 μm to raise the powder to liquid ratio and express a high elastic modulus. On the other hand, when the dental glass ionomer cement composition of the present invention is used as a material for luting, the 50% particle size (D50) of the acid reactive glass powder is preferably in a range from 0.5 to 10 μm, more preferably 0.5 to 5 μm to express a thin coating thickness.

When the 50% particle size (D50) of the acid reactive glass powder is less than 0.5 μm, its surface area increases not to be able to contain a large amount in the composition, and thereby its mechanical property may be reduced. Furthermore, operation surplus time may be shortened.

When the 50% particle size (D50) of the acid reactive glass powder exceeds 15 μm, the surface of the material becomes rough after polishing, and there is a possibility that the acid reactive glass powder is easily colored within a mouth in the case of using it for filling. Furthermore, in the case of using it for luting, coating thickness becomes thick, luted and/or adhered prosthesis equipment becomes floating, and adaptation of the intended prosthesis equipment may no longer be obtained.

As the hydrophobizing surface treatment agent which can be used upon producing the hydrophobized acid reactive glass powder (a), known hydrophobizing surface treatment agents can be used. Specifically, examples of the hydrophobizing surface treatment agent include a silane coupling agent, an organosilazane, a titanate coupling agent, a zirconium coupling agent, and an aluminate coupling agent. These hydrophobizing surface treatment agents can be used alone or in a combination of a few kinds. Among these hydrophobizing surface treatment agents, a silane coupling agent, or an organosilazane is preferably used.

The hydrophobizing surface treatment agent may be at least one kind of hydrophobizing surface treatment agents selected from a silane coupling agent represented by the general formula (1):

$$R_nSiA_{4-n} \qquad (1)$$

wherein R is a hydrocarbon group with carbon number of 1 to 20 which may have substituent(s), A represents an alkoxy group with carbon number of 1 to 4, an alkoxyalkoxy group with carbon number of 2 to 10, an acyloxy group with carbon number of 1 to 6, an alkenyloxy group with carbon number of 2 to 6, a halogen atom, an isocyanate group, a hydroxy group, or a hydrogen atom, and n is an integer of 1 to 3, provided that a plurality of R and A may be the same or differ from each other, and an organosilazane represented by the general formula (2):

$$R^1R^2R^3\text{—Si—NH—Si—}R^4R^5R^6 \qquad (2)$$

wherein $R^1$, $R^2$, and $R^3$ are independently a hydrogen atom or a hydrocarbon group with carbon number of 1 to 6 which may have substituent(s), at least one of $R^1$, $R^2$, and $R^3$ is a hydrocarbon group with carbon number of 1 to 6 which may have substituent(s), $R^4$, $R^5$, and $R^6$ are independently a hydrogen atom, or a hydrocarbon group with carbon number of 1 to 6 which may have substituent(s), and at least one of $R^4$, $R^5$, and $R^6$ is a hydrocarbon group with carbon number of 1 to 6 which may have substituent(s). In such the case, the mixing efficiency and/or mechanical property are easy to be improved.

As aforementioned, examples of the silane coupling agent include the following general formula (1):

$$R_nSiA_{4-n} \qquad (1)$$

wherein R is a hydrocarbon group with carbon number of 1 to 20 which may have substituent(s), A represents an alkoxy group with carbon number of 1 to 4, an alkoxyalkoxy group with carbon number of 2 to 10, an acyloxy group with carbon number of 1 to 6, an alkenyloxy group with carbon number of 2 to 6, a halogen atom, an isocyanate group, a hydroxy group, or a hydrogen atom, and n is an integer of 1 to 3, provided that a plurality of R and A may be the same or differ from each other.

Examples of the hydrocarbon group R include an alkyl group with carbon number of 1 to 20, a cycloalkyl group with carbon number of 3 to 20, an alkenyl group with carbon number of 2 to 20, and an aryl group with carbon number of 6 to 20. For example, examples of the alkyl group include methyl group, ethyl group, n-propyl group, isopropyl group, n-butyl group, isobutyl group, sec-butyl group, tert-butyl group, n-pentyl group, isopentyl group, neopentyl group, n-hexyl group, n-heptyl group, n-octyl group, 2-ethylhexyl group, n-nonyl group, n-decyl group, n-undecyl group, n-dodecyl group, n-tetradecyl group, n-hexadecyl group, and eicosyl group. Examples of the cycloalkyl group include cyclopropyl group, cyclopentyl group, and cyclohexyl group. Examples of the alkenyl group include vinyl group, allyl group, 1-propenyl group, 1-methylethenyl group, 1-butenyl group, 2-butenyl group, 3-butenyl group, 1-pentenyl group, 2-pentenyl group, 4-pentenyl group, 1-hexenyl group, 1-heptenyl group, 1-octenyl group, 1-nonenyl group, 1-decenyl group, 1-undecenyl group, and 1-dodecenyl group. Examples of the aryl group include phenyl group, tolyl group, xylyl group, naphthyl group, and biphenyl group. Examples of the substituent(s) of the aforementioned hydrocarbon group include an acetyl group, an acetoxy group, a methacryloyl group, acryloyl group, an alkoxy group with carbon number of 1 to 6, a phenoxy group, an alkylamino group with carbon number of 1 to 6, a phenylamino group, and a halogen atom.

Examples of the alkoxy group with carbon number of 1 to 4 of A include methoxy group, ethoxy group, n-propoxy group, isopropoxy group, n-butoxy group. Examples of the alkoxyalkoxy group with carbon number of 2 to 10 include methoxymethoxy group, methoxyethoxy group, 3-methoxy-n-propoxy group, and 4-methoxy phenoxy group. Examples of the acyloxy group with carbon number of 1 to 6 include acetoxy group, ethylcarbonyloxy group, propylcarbonyloxy group, isopropylcarbonyloxy group, and benzoyloxy group. Examples of the alkenyloxy group with carbon number of 2 to 6 include isopropenoxy group, 2-propenoxy group, 2-butenoxy group, and 3-butenoxy group.

The silane coupling agent of the general formula (1) is illustrated specifically. In addition, in the following illustrations, both of acryloyl and methacryloyl are comprehensively represented by (meth)acryloyl. Examples of the silane coupling agent of the general formula (1) include methyltrimethoxysilane, methyltriethoxysilane, dimethyldimethoxysilane, dimethyldiethoxysilane, ethyltrimethoxysilane, ethyltriethoxysilane, diethyldiethoxysilane, methyltrichlorosilane, dimethyldichlorosilane, trimethylchlorosilane, trimethylsilanol, methoxytripropylsilane, methyltri-n-propoxysilane, dimethoxydiphenylsilane, phenyltrimethoxysilane, phenyltriethoxysilane, phenyltrichlorosilane, diphenyldichlorosilane, diphenyldimethoxysilane, diphenyldiethoxysilane, diethylsilane, methyltris(2-methoxyethoxy)silane, n-propyltrimethoxysilane, n-propyltriethoxysilane, isobutyltrimethoxysilane, n-butyltrimethoxysilane, hexyltrimethoxysilane, hexyltriethoxysilane, n-decyltriethoxysilane, cyclopentyltrimethoxysilane, cyclohexylethyldimethoxysilane, cyclohexyltrimethoxysilane, vinyltrimethoxysilane, vinyltriethoxysilane, vinyltrichlorosilane, vinylacetoxysilane, vinyltris(β-methoxyethoxy)silane, p-styryltrimethoxysilane, N-phenyl-γ-aminopropyltrimethoxysilane, styrylethyltrimethoxysilane, p-tolyltrimethoxysilane, 3-methoxypropyltrimethoxysilane, allyltriethoxysilane, allyltrimethoxysilane, 3-butenyltriethoxysilane, benzyltriethoxysilane, 3-(meth)acryloyloxypropyltrimethoxysilane, 3-(meth)acryloyloxypropyltriethoxysilane, 6-(meth)acryloyloxyhexyltrimethoxysilane, 6-(meth)acryloyloxyhexyltriethoxysilane, 10-(meth)acryloyloxydecyltrimethoxysilane, 10-(meth)acryloyloxydecyltriethoxysilane, 11-(meth)acryloyloxyundecyltrimethoxysilane, 11-(meth)acryloyloxyundecyltriethoxysilane, 3-(meth)acryloyloxypropylmethyldiethoxysilane, 3-(meth)acryloyloxypropylmethyldimethoxysilane, 3-(meth)acryloyloxypropyltris(2-methoxyethoxy)silane, chloromethyltriethoxysilane, chloromethyltrimethoxysilane, chlorophenyltriethoxysilane, 2-chloroethyltrimethoxysilane, 3-chloropropyltrimethoxysilane, 3,3,3-trifluoropropyltrimethoxysilane, methyl-3,3,3-trifluoropropyldimethoxysilane, and 2-chloroethylmethyldimethoxysilane.

As aforementioned, examples of the organosilazane include the following general formula (2):

$$R^1R^2R^3-Si-NH-Si-R^4R^5R^6 \quad (2)$$

wherein $R^1$, $R^2$, and $R^3$ are independently a hydrogen atom, or a hydrocarbon group with carbon number of 1 to 6 which may have substituent(s), at least one of $R^1$, $R^2$, and $R^3$ is a hydrocarbon group with carbon number of 1 to 6 which may have substituent(s), $R^4$, $R^5$, and $R^6$ are independently a hydrogen atom, or a hydrocarbon group with carbon number of 1 to 6 which may have substituent(s), and at least one of $R^4$, $R^5$, and $R^6$ is a hydrocarbon group with carbon number of 1 to 6 which may have substituent(s).

Examples of the hydrocarbon group with carbon number of 1 to 6, which may have substituent(s) of $R^1$, $R^2$, $R^3$, $R^4$, $R^5$, and $R^6$, include methyl group, ethyl group, n-propyl group, isopropyl group, n-butyl group, isobutyl group, sec-butyl group, tert-butyl group, n-pentyl group, isopentyl group, neopentyl group, n-hexyl group, vinyl group, allyl group, and phenyl group.

By specifically illustrating the organosilazane of the general formula (2), its examples include 1,1,1,3,3,3-hexamethyldisilazane, 1,1,1,3,3,3-hexaethyldisilazane, 1,3-divinyl-1,1,3,3-tetramethyldisilazane, 1,1,1,3,3,3-hexaphenyldisilazane, 1,1,1,3,3,3-hexaisopropylsilazane, 1,1,1,3,3,3-hexan-propyldisilazane, 1,1,1,3,3,3-hexabutyldisilazane, 1,3-diethyl-1,1,3,3-tetramethyldisilazane, 1,3-diphenyl-1,1,3,3-tetramethyldisilazane, 1,3-dimethyl-1,1,3,3-tetraphenyldisilazane, 1,3-dipropyl-1,1,3,3-tetramethyldisilazane, and 1,1,3,3-tetramethyldisilazane.

Examples of the titanate coupling agent include tetramethyl titanate, tetraethyl titanate, tetraisopropyl titanate, tetra-n-butyl titanate, tetraisobutyl titanate, butyl titanate dimer, tetra(2-ethylhexyl) titanate, tetraoctyl titanate, tetrastearyl titanate, tetraisostearyl titanate, isopropyltriisostearoyltitanate, isopropyltrioctanoly titanate, isopropyldimethacrylisostearoyl titanate, and isopropylisostearoyldiacryl titanate.

Examples of the zirconium coupling agent include zirconium n-butoxide, zirconium n-propoxide, zirconium isopropoxide, zirconium acetylacetonate, zirconium tributoxystearate, zirconium dibutoxybis(acetylacetonate), zirconium tributoxyethylacetoacetate, and zirconium butoxyacetylacetonate bis(ethylacetoacetate).

Examples of the aluminate coupling agent include aluminium acetylacetonate, acetoalkoxyaluminium diisopropylate, diisopropoxyaluminium ethylacetoacetate, diisopropoxyaluminium alkylacetoacetate, and diisopropoxyaluminium monomethacrylate.

The surface treatment method of the acid reactive glass powder using the hydrophobizing surface treatment agent is not particularly limited, and known methods can be used. For example, examples of the surface treatment method include a method of spraying the hydrophobizing surface treatment agent diluted with a suitable solvent while agitating the acid reactive glass powder in a mixing vessel, and mixing within the vessel, and then heat treating them; a method of dissolving and mixing the hydrophobizing surface treatment agent in a slurry in which the acid reactive glass powder is distributed in a suitable solvent, and then carring out a solvent distillation and heat treatment, or a spray dry; and a method of dissolving the hydrophobizing surface treatment agent into a slurry in which the acid reactive glass powder is distributed in the suitable solvent, refluxing them, and then carrying out a solvent distillation and heat treatment. In addition, a hydrophobizing surface treatment agent can also be used after prehydrolyzing it in a solvent containing a water in which the acid catalyst etc. is optionally added or containing water, if necessary. Furthermore, in any of the surface treatment methods, although the temperature upon heat-treating is not particularly limited, the temperature is preferably in a range from 50 to 200° C., and more preferably a range from 100 to 150° C.

The hydrophobized acid reactive glass powder (a) of the dental glass ionomer cement composition may be hydrophobization-treated by 0.05 to 3.0% by parts of a hydrophobizing surface treatment agent based on 100 parts by mass of an acid reactive glass powder. In such the case, the mixing efficiency and/or mechanical property are easy to be improved.

The treating amount of the hydrophobizing surface treatment agent to the acid reactive glass powder is preferably in a range from 0.05 to 3.0 parts by mass, more preferably the range of 0.1 to 1.5 parts by mass, still more preferably the range of 0.2 to 1.0 parts by mass based on the acid reactive glass powder 100 parts by mass. When the treating amount of the hydrophobizing surface treatment agent to the acid reactive glass powder 100 parts by mass is less than 0.05 parts by mass, the mixing efficiency of the powder and the liquid in the mechanical mixing, may not be improved, and it may cause the reduction of the shortage of mixing, or the mechanical property. Furthermore, when the treating amount of the hydrophobizing surface treatment agent exceeds 3.0 parts by mass, an acid-base reaction with the polyalkene acid (b) may be inhibited to reduce its mechanical property.

Furthermore, for the purpose of adjusting the operativity, setting property, or mechanical property, etc. of the dental glass ionomer cement composition of the present invention, a surface treatment, heat treatment or aggregation treatment in a liquid or gas phase, etc. using a different surface treatment agent (hereinafter referred to as other surface treatment agents) can be carried out without any problems even in a combination with a surface treatment upon producing the aforementioned hydrophobized acid reactive glass powder (a) as an optional treatment for the acid reactive glass powder in a range in which the acid-base reaction with the polyalkene acid (b) is not affected. These optional treatments can be carried out alone or complexly in a few kinds, and further the order of carrying out each treatment is not particularly limited. Since it is easy to control various properties and its productivity is excellent, the surface treatment using other surface treatment agents, or the heat treatment among them is suitable.

By specifically illustrating the optional surface treatment of the acid reactive glass powder using other surface treatment agents, its examples include a washing with an acid such as phosphoric acid or acetic acid, a surface treatment by an acidic compound such as tartaric acid or polycarboxylic acid, a surface treatment by a fluoride such as aluminium fluoride, and the surface treatment by a silane compound such as a partially hydrolyzed oligomer of tetramethoxysilane, tetraethoxysilane or tetramethoxysilane, and a partially hydrolyzed oligomer of tetraethoxysilane. The surface treatment method which can be used in the present invention is not limited to the aforementioned methods, and these surface treatment methods can be respectively used alone or complexly in a combination.

By specifically illustrating the heat treatment method of the acid reactive glass powder, its examples include a treatment method of heating the acid reactive glass powder in a range from 200° C. to 800° C. for 1 hour to 72 hours using an electric furnace, etc. The heat treatment method which can be used in the present invention is not limited to the aforementioned methods, and a single treatment or multistage treatment, etc. is also possible for its treatment process.

The dental glass ionomer cement composition of the present invention may comprises, based on the total dental glass ionomer cement composition,
(a) a hydrophobized acid reactive glass powder 54.5 to 80.0% by mass,
(b) a polyalkene acid 5.8 to 27.3% by mass, and
(c) water 7.6 to 27.3% by mass. In such the case, the mixing efficiency and/or mechanical property are easy to be improved.

The hydrophobized acid reactive glass powder (a) is preferably contained at 54.5 to 80.0% by mass based on the total dental glass ionomer cement composition of the present invention. When the content of the hydrophobized acid reactive glass powder (a) is less than 54.5% by mass, its mechanical property may be reduced. Furthermore, when the content of the hydrophobized acid reactive glass powder (a) exceeds 80.0% by mass, there is the case where operation surplus time is shortened, or where a uniform cement mixture is not obtained and its mechanical property may be reduced.

In addition, the dental glass ionomer cement composition of the present invention can contain an acid reactive glass powder which is not surface treated by the hydrophobizing surface treatment agent although not essentially for the purpose of adjusting the mechanical property and the setting property if its content is within a range which does not have a harmful influence on the mixing efficiency in the mechanical mixing. In this case, a blending ratio of the hydrophobized acid reactive glass powder (a) contained in the dental glass ionomer cement composition of the present invention to the acid reactive glass powder is preferably within a range from 70:30 to 99:1 in a mass ratio.

Further, the dental glass ionomer cement composition of the present invention may be constituted from a powder and a liquid, wherein the powder and the liquid are separately packaged in a dental capsule, and wherein the hydrophobized acid reactive glass powder (a) is contained in the powder, the water (c) is contained in the liquid, and the polyalkene acid (b) is contained in the powder and/or the liquid.

Such the composition is not only easy to improve the mixing efficiency and/or mechanical property without reducing fluoride-release property, and but also may be more suitable for practical use (in particular, use in a mechanical mixing equipment).

If the polyalkene acid (b) which can be used for the dental glass ionomer cement composition of the present invention is a homopolymer or copolymer of an alkene acid at least having one or more carboxy groups in its molecule, such as an unsaturated monocarboxylic acid, an unsaturated dicarboxylic acid, and an unsaturated tricarboxylic acid, the polyalkene acid can be used without any restrictions. Furthermore, even if the polyalkene acid (b) is a copolymer of a polymerizable monomer and an alkene acid having no acidic group in a molecule, the polyalkene acid is satisfactory at all.

By specifically illustrating the alkene acid which can be used to obtain the polyalkene acid (b), its examples include acrylic acid, methacrylic acid, 2-chloroacrylic acid, 3-chloroacrylic acid, 2-cyanoacrylic acid, aconitic acid, mesaconic acid, maleic acid, maleic anhydride, itaconic acid, itaconic acid anhydride, fumaric acid, glutaconic acid, citraconic acid, utraconic acid, 1-butene-1,2,4-tricarboxylic acid, and 3-butene-1,2,3-tricarboxylic acid, but is not limited thereto. Among them, a polyalkene acid (b) which is synthesized from only acrylic acid as a starting material, or a polyalkene acid (b) which is synthesized from two or more kinds of alkene acids, such as acrylic acid and maleic acid, acrylic acid and maleic anhydride, acrylic acid and itaconic acid, and acrylic acid and 3-butene-1,2,3-tricarboxylic acid, etc. as a starting material, can be preferably used.

The polymerization method used to obtain the various polyalkene acids (b) is not particularly limited, and polyalkene acids which were polymerized by any methods, such as solution polymerization, suspension polymerization, and emulsion polymerization, can be used without any restrictions. Furthermore, the polymerization initiator or a chain transfer agent to be used upon synthesis of the polymer can be appropriately selected to obtain a desired polymer. Such the obtained polyalkene acid (b) can be used alone or in a combination of a few kinds.

The weight average molecular weight of the polyalkene acid (b) is preferably within a range from 30,000 to 300,000. And, the weight average molecular weight refers to an average molecular weight calculated based on a molecular weight distribution as measured by gel permeation chromatography. When the weight average molecular weight of the polyalkene acid (b) is less than 30,000, its mechanical property may be reduced. Furthermore, when the weight average molecular weight of the polyalkene acid (b) exceeds 300,000, there is the case where operation surplus time is shortened, or where a uniform cement mixture is not obtained and its mechanical property may be reduced.

The polyalkene acid (b) is preferably contained at 5.8 to 27.3% by mass based on the total dental glass ionomer cement composition of the present invention. When the content of the polyalkene acid (b) is less than 5.8% by mass, its mechanical property may be reduced. Furthermore, when the content of the polyalkene acid (b) exceeds 27.3% by mass, there is the case where operation surplus time is shortened, or where a uniform cement mixture is not obtained and its mechanical property may be reduced.

The water (c) which can be used for the dental glass ionomer cement composition of the present invention, is an essential component to diffuse a metal ion eluted from the hydrophobized acid reactive glass powder (a) to induce a crosslinking reaction with the polyalkene acid (b), along with functioning as a solvent for dissolving the polyalkene acid (b).

As the water (c), a water which does not contain an impurity having a harmful influence on curability and mechanical property in the dental glass ionomer cement composition of the present invention, can be used without any restrictions. Namely, a water which can start the acid-base reaction of the dental glass ionomer cement composition can be used without any restrictions. For example, distilled water or ion exchange water can be used.

The water (c) is preferably contained at 7.6 to 27.3% by mass based on the total dental glass ionomer cement composition of the present invention. When the content of the water (c) is less than the 7.6% by mass, there is the case where operation surplus time is shortened, or where a uniform cement mixture is not obtained and its mechanical property may be reduced. Furthermore, when the content of the water (c) exceeds 27.3% by mass, there is the case where its mechanical property may be reduced.

The dental glass ionomer cement composition of the present invention can optionally contain acidic compound(s) although not essentially for the purpose of adjusting the operation surplus time and the curing time. The kind of the acidic compound(s) is not particularly limited. By specifically illustrating these acidic compounds, their examples include carboxylic acid compounds such as tartaric acid, citric acid, maleic acid, fumaric acid, malic acid, aconitic acid, tricarballylic acid, itaconic acid, 1-butene-1,2,4-tricarboxylic acid and 3-butene-1,2,3-tricarboxylic acid; phosphoric acid compounds, such as phosphoric acid, pyrophosphoric acid, and tripolyphosphoric acid; and metal salts of these acidic compounds, and are not limited to these acidic compounds. These acidic compounds can be used alone or in a combination of a few kinds. In the case where the acidic compound is contained, the acidic compound is preferably contained in a range from the 0.1 to 15% by mass based on the total dental glass ionomer cement composition of the present invention.

Furthermore, the dental glass ionomer cement composition of the present invention can optionally but not essentially contain a surfactant for the purpose of adjusting an early adaptation of the powder and the liquid or a property of their cement mixture in a range which does not affect various properties. The surfactant which can be used for the dental glass ionomer cement composition of the present invention may be any of ionic surfactants and nonionic surfactants.

By specifically illustrating the ionic surfactants, their examples include, as anionic surfactants, aliphatic carboxylic acid metal salts such as sodium stearate, etc., sulfated aliphatic carboxylic acid metal salts such as sodium dioctyl sulfosuccinate, etc., and metal salts of higher alcohol sulfate esters such as stearylsulfate ester sodium. Furthermore, their examples include, as cationic surfactants, an adduct of a higher alkylamine and ethyleneoxide, amines made from a lower amine, and alkyl trimethylammonium salts such as lauryl trimethyl ammonium chloride, etc. Furthermore, their examples include, as amphoteric surfactants, metal salts of higher alkyl aminopropionic acids such as sodium stearylaminopropionate, etc. and betaines such as lauryl dimethylbetaine, etc.

Examples of the nonionic surfactant, furthermore, include polyethylene glycol types or polypropylene glycol types in which ethylene oxide or propylene oxide is added to higher alcohols, alkylphenols, fatty acids, higher fatty amines, or aliphatic amides, etc., or polyhydric alcohol types in which a fatty acid is ester bonded with polyhydric alcohols, diethanolamines, or saccharides.

The aforementioned surfactants are not limited to these surfactants, and can be used without any restrictions. Furthermore, these surfactants can be used alone or in a combination of a few kinds.

In the case where the surfactant is contained in the dental glass ionomer cement composition of the present invention, the surfactant is preferably contained in a range from 0.001 to 5% by mass based on the total dental glass ionomer cement composition.

Furthermore, the dental glass ionomer cement composition of the present invention can optionally but not essentially contain a non-acid reactive powder for the purpose of adjusting the operation, the mechanical property and the curing property if its content is within a range which does not have a harmful influence on the various properties.

The non-acid reactive powder which can be used for the dental glass ionomer cement composition of the present invention can be used without being particularly limited if the element to be reacted with the acidic group which the polyalkene acid (b) has is not included. Examples of the non-acid reactive powder include those which is known as a dental filler, for example, an inorganic filler, an organic filler, organic-inorganic composite filler, and these non-acid reactive powders can be used alone or in a combination of a few kinds. Among them, the inorganic filler is preferably used. Furthermore, the shape of these non-acid reactive powders are not particularly limited, and the shape of the non-acid reactive powders may be an arbitrary particle shape, such as a globular, needle, tabular, granular, or scale shape, or their aggregates, and is not limited to these shapes.

Although the average particle size of these non-acid reactive powders is not particularly limited, it is preferably in a range from 0.001 to 30 μm.

By specifically illustrating the inorganic filler, its examples include quartz, amorphous silica, ultrafine particle silica, various glasses which do not contain an element which is reacted with an acidic group (which include a glass by scorification, a synthetic glass by a sol-gel method, a glass generated by a gas phase reaction, etc.), silicon nitride, silicon carbide, and boron carbide, and it is not limited to these inorganic fillers.

In the case where the non-acid reactive powder is contained in the dental glass ionomer cement composition of the present invention, the non-acid reactive powder is preferably contained in a range from 0.001 to 20% by mass based on the total dental glass ionomer cement composition.

Furthermore, the dental glass ionomer cement composition of the present invention can optionally but not essentially include components, such as antiseptic agents, antibacterial agents, coloring agents, fluorescence agents, inorganic fiber materials, organic fiber materials, and other conventionally known additives, if necessary.

In the dental glass ionomer cement composition of the present invention, its essential components can be divided into a powder and a liquid in various combinations unless the hydrophobized acid reactive glass powder (a) and the polyalkene acid (b) exist together under the presence of the water (c). By specifically illustrating the combinations, their examples include:

a combination of the powder containing the hydrophobized acid reactive glass powder (a) and the liquid containing the polyalkene acid (b) and the water (c), a combination of the powder containing the hydrophobized acid reactive glass powder (a) and the polyalkene acid (b) and the liquid containing the water (c), and a combination of the powder containing the hydrophobized acid reactive glass powder (a) and the polyalkene acid (b) and the liquid containing the polyalkene acid (b) and the water (c).

The powder to liquid ratio in the dental glass ionomer cement composition of the present invention refers to a mass ratio of powder to liquid (powder mass/liquid mass), the powder to liquid ratio is not particularly limited, and the powder to liquid ratio is preferably in a range from 1.0/1.0 to 6.0/1.0, more preferably in a range from 1.2/1.0 to 4.0/1.0.

The dental glass ionomer cement composition of the present invention can be used for a wide range of uses in dental treatment such as a pit and fissure plugging material, a lining material, an abutment construction material, etc., in addition to the use as a filling material and a luting agent.

EXAMPLES

Hereinafter, although Examples specifically explain the present invention, the present invention is not limited to these Examples. Test methods upon evaluating the performance of the dental glass ionomer cement composition used for Examples and Comparative Examples are as follows.
[Preparation of Cement Mixture]
<Mechanical Mixing>

Under an environment at 23° C. and a humidity of 50%, a predetermined amount of a powder and a liquid were filled into a dental capsule. In addition, the filling amount of the liquid was unified into 115 mg, and the filling amount of the powder was determined according to the powder to liquid ratio set in each of Examples and Comparative Examples, respectively. After releasing the liquid within the dental capsule container, the dental capsule was set in the capsule mixer (Ultramat2/manufactured by SDI Limited, a rotation speed of 4000 rpm or more), and was mixed for 10 seconds. The cement mixture was discharged from the nozzle of the dental capsule using the applicator, and was provided in each test.
<Hand Mixing>

After measuring a proper amount of a powder and a liquid on a mixing pad under an environment of 23° C. and a humidity of 50% according to a predetermined powder to liquid ratio, and was mixed for about 30 seconds using a plastic spatula, and was provided in each test.

In addition, in any cases of the mechanical mixing and the hand mixing, those having a powder to liquid ratio of 2.2/1.0 or more were tested as the filling materials, and those having a powder to liquid ratio of less than 2.2/1.0 were tested as the luting materials.
[Mixing Property]

Under an environment of 23° C. and a humidity of 50%, cement mixture immediately after mixing were visually checked to evaluate their mixing property in accordance with the following evaluation criteria. In addition, when the evaluation was ⊚ or Δ in the present description, it was decided that the cement mixture had good mixing property.
[Evaluation Criteria]

⊚: Remaining of a powder is not observed in the cement mixture.

Δ: A powder slightly remains in the cement mixture (It is observed that the powder remains at a filled powder content of 2% or less in the cement mixture).

X: A lot of a powder remains in the cement mixture (It is observed that the powder remains at a filled powder content of more than 2% in the cement mixture).
[Compressive Strength]

According to ISO 9917-1:2007, compressive strength was measured as a mechanical property by the following procedure. After the cement mixture was filled into a stainless steel metal mold (column shape having inside diameter: 4 mm and height: 6 mm) under an environment of 23° C. and a humidity of 50%, and was left to stand into a thermostatic and humidiying vessel at 37° C. and a humidity of 100%. A setting material was removed from the metal mold after standing for 1 hour, and was made as the specimens. After the specimens was immersed into ion exchange water at 37° C. for 24 hours from the end of mixing, compressive strength was measured under a condition of crosshead speed 1 mm/min. using an instron universal testing machine (Type: 5567A) for the specimens.

Further, from the measurement results of the compressive strength, evaluations on performance were carried out according to the following evaluation criteria.

In addition, it was decided that when in the present description, any of the filling material and the luting material have evaluations of from ⊚ to ▲, they have good compressive strength (namely, have a high mechanical property).
[Evaluation]
—Evaluation Criteria—
[Filling Material]

⊚: Compressive strength is 230 MPa or more.
○: Compressive strength is 220 MPa or more and less than 230 MPa.
Δ: Compressive strength is 210 MPa or more and less than 220 MPa.
▲: Compressive strength is 200 MPa or more and less than 210 MPa.
X: Compressive strength is less than 200 MPa.

[Luting Material]
◎: Compressive strength is 170 MPa or more.
○: Compressive strength is 160 MPa or more and less than 170 MPa.
Δ: Compressive strength is 150 MPa or more and less than 160 MPa.
▲: Compressive strength is 140 MPa or more and less than 150 MPa.
X: Compressive strength is less than 140 MPa.

[Fluoride-Release Property]

After the cement mixture was filled into a stainless steel metal mold (disk shape having an inside diameter: 12 mm and a thickness: 1 mm) under an environment of 23° C. and a humidity of 50%, and was left to stand into a thermostatic and humidiying vessel at 37° C. and a humidity of 100%. A setting material was removed from the metal mold after standing for 1 hour, and was immersed into distilled water (5 mL) at 37° C. A setting material was removed after one-week immersion, and the fluoride ion concentration in a fluoride ion eluate was measured using a fluoride ion combination electrode (Model 96-09: Orion Research Co.) and an ion meter (Model 720A: Orion Research Co.). A measurement of the fluoride ion concentration was carried out after 0.5 mL of an ionic strength regulator (TISABIII, Orion Research Co.) was added to the fluoride ion eluate.

Further, from the measurement results of the fluoride-release property, evaluations on performance were carried out according to the following evaluation criteria.

In addition, it was decided that when in the present description, the cement mixture have evaluations of from ◎ to Δ, they have excellent fluoride-release property.

[Evaluation]
—Evaluation Criteria—
◎: Fluoride-release property is 25 ppm or more.
○: Fluoride-release property is 20 ppm or more and less than 25 ppm.
Δ: Fluoride-release property is 15 ppm or more and less than 20 ppm.
X: Fluoride-release property is less than 15 ppm

[Total Evaluation]

As a result of evaluating the aforementioned performances, the inventors decided that those which exhibited a good mixing property, a high compressive strength, and an excellent fluoride-release property had properties desirable as the dental glass ionomer cement composition.

Specifically, from the evaluations or measurement results on compressive strength, mixing property and fluoride-release property, total evaluations on performances were carried out based on total values by scoring according to the following evaluation criteria:

—Evaluation Criteria—

Each score on evaluation results for compressive strength, mixing property and fluoride-release property are:

◎: 4 poins, ○: 3 poins, Δ: 2 poins, ▲: 1 point, or X: 0 poins.

—Classification of Total Evaluations—
A (Very good): 12 points
B: 11 points
C: 10 points
D (Good): 9 points
E: 8 points
F: 7 points
G: 6 points
H (Somewhat good): 5 points
I (Poor) not more than 4 points, or one or more of X is included in evaluations of each test.

Production methods of the dental glass ionomer cement compositions used for Examples and Comparative Examples were shown below.

[Production of Acid Reactive Glass Powders]

[Production of Acid Reactive Glass Powder 1 (G1)]

After mixing at a rate of 23% by mass of silica, 8% by mass of aluminium oxide, 13% by mass of aluminium phosphate, 14% by mass of aluminium fluoride, and 42% by mass of strontium carbonate, they were melted and a melted solution was quenched in water to obtain a glass. The resulting glass was pulverized to obtain an acid reactive glass powder 1 (G1). The 50% particle size (D50) of this acid reactive glass powder was 4.7 μm as a result of measuring with a laser diffraction particle size measuring apparatus (Microtrack MT3300EXII: manufactured by Microtrack Bell Co.).

[Production of Acid Reactive Glass Powders 2 to 8 (G2 to G8)]

These acid reactive glass powders were produced by the same method as that in the acid reactive glass powder 1 (G1) except for adjusting to 50% particle size (D50) shown in Table 1 by changing the pulverizing time.

TABLE 1

| Acid reactive glass powders 1 to 8 (G1 to G8) | | | | | | | | |
|---|---|---|---|---|---|---|---|---|
| | G1 | G2 | G3 | G4 | G5 | G6 | G7 | G8 |
| 50% particle size (D50) (μm) | 4.7 | 0.4 | 0.5 | 15.0 | 15.4 | 3.0 | 5.0 | 10.0 |

[Production of (a) Hydrophobized Acid Reactive Glass Powders]

[Production of Hydrophobized Acid Reactive Glass Powder 1 (TG1)]

0.3 g of γ-methacryloyloxy-propyltrimethoxysilane, 0.1 g of an ion exchange water, and 8.8 g of anhydrous ethanol were mixed to prepare a surface treating liquid (total mass: 9.2 g). After mixing this surface treating liquid with 100 g of the acid reactive glass powder 1 (G1) in a dry form, the mixture were heat treated at 110° C. for 5 hours using a hot air drying equipment to obtain a hydrophobized acid reactive glass powder 1 (TG1).

[Production of Hydrophobized Acid Reactive Glass Powders 2 to 18 (TG2 to TG18)]

These hydrophobized acid reactive glass powders were produced by the same method as that in the hydrophobized acid reactive glass powder 1 (TG1) except for modifying to acid reactive glass powders, surface treatment agents, and their treating amounts, as shown in Tables 2 and 3. In addition, the surface treating liquids used upon producing each of hydrophobized acid reactive glass powders, were prepared according to the following. Namely, ion exchange water was added to the amount of each of the surface treatment agents as shown in Table 2 and 3 such that the surface treatment agents: ion exchange water=3:1 (mass ratio), and anhydrous ethanol was added such that the total mass becomes 9.2 g similarly to the surface treating liquid used for production of the hydrophobized acid reactive glass powder 1 (TG1), and then mixed to prepare each surface treating liquid.

TABLE 2

(a) Hydrophobized acid reactive glass powders 1 to 10 (TG1 to TG10) (units: g)

|  |  | TG1 | TG2 | TG3 | TG4 | TG5 | TG6 | TG7 | TG8 | TG9 | TG10 |
|---|---|---|---|---|---|---|---|---|---|---|---|
| Acid reactive glass powders | 50% particle size (D50) (μm) | 4.7 | 0.4 | 0.5 | 15.0 | 15.4 | 4.7 | 4.7 | 4.7 | 4.7 | 0.5 |
|  | G1 | 100.00 | — | — | — | — | 100.00 | 100.00 | 100.00 | 100.00 | — |
|  | G2 | — | 100.00 | — | — | — | — | — | — | — | — |
|  | G3 | — | — | 100.00 | — | — | — | — | — | — | 100.00 |
|  | G4 | — | — | — | 100.00 | — | — | — | — | — | — |
|  | G5 | — | — | — | — | 100.00 | — | — | — | — | — |
|  | G6 | — | — | — | — | — | — | — | — | — | — |
|  | G7 | — | — | — | — | — | — | — | — | — | — |
|  | G8 | — | — | — | — | — | — | — | — | — | — |
| Surface treatment agent | γ-Methacryloyloxypropyl trimethoxysilane | 0.30 | 3.10 | 3.00 | 0.05 | 0.04 | — | — | — | — | 0.05 |
|  | Vinyltrimethoxysilane | — | — | — | — | — | 0.30 | — | — | — | — |
|  | 1,1,1,3,3,3-Hexamethyldisilazane | — | — | — | — | — | — | 0.30 | — | — | — |
|  | Phenyltriethoxysilane | — | — | — | — | — | — | — | 0.30 | — | — |
|  | γ-Aminopropyltrimethoxysilane[i) | — | — | — | — | — | — | — | — | 0.30 | — |

[i)] Since the present compound is not a hydrophobizing surface treatment agent, the surface treated acid reactive glass powder does not exhibit a hydrophobicity.

TABLE 3

(a) Hydrophobized acid reactive glass powders 11 to 18 (TG11 to TG18) (units: g)

|  |  | TG11 | TG12 | TG13 | TG14 | TG15 | TG16 | TG17 | TG18 |
|---|---|---|---|---|---|---|---|---|---|
| Acid reactive glass powder | 50% particle size (D50) (μm) | 15.0 | 4.7 | 3.0 | 15.0 | 0.5 | 5.0 | 0.5 | 10.0 |
|  | G1 | — | 100.00 | — | — | — | — | — | — |
|  | G2 | — | — | — | — | — | — | — | — |
|  | G3 | — | — | — | — | 100.00 | — | 100.00 | — |
|  | G4 | 100.00 | — | — | 100.00 | — | — | — | — |
|  | G5 | — | — | — | — | — | — | — | — |
|  | G6 | — | — | 100.00 | — | — | — | — | — |
|  | G7 | — | — | — | — | — | 100.00 | — | — |
|  | G8 | — | — | — | — | — | — | — | 100.00 |
| Surface treatment agent | γ-Methacryloyloxypropyl trimethoxysilane | 3.00 | 5.00 | 1.00 | 0.20 | 1.00 | 0.20 | 1.50 | 0.10 |
|  | Vinyltrimethoxysilane | — | — | — | — | — | — | — | — |
|  | 1,1,1,3,3,3-Hexamethyldisilazane | — | — | — | — | — | — | — | — |
|  | Phenyltriethoxysilane | — | — | — | — | — | — | — | — |
|  | γ-Aminopropyltrimethoxysilane[i)] | — | — | — | — | — | — | — | — |

[i)] Since the present compound is not a hydrophobizing surface treatment agent, the surface treated acid reactive glass powder does not exhibit a hydrophobicity.

[(b) Polyalkene Acid]
PCA1: Acrylic acid-tricarboxylic acid copolymer powder (Weight average molecular weight: 80,000)
PCA2: Acrylic acid homopolymer powder (Weight average molecular weight: 100,000)
[(c) Water]
IEW: Ion exchange water
[Other Component]
TA: Tartaric acid

[Preparation of Powders and Liquids]

Compositions of the powders P1 to P22 were shown in Tables 4 and 5. In the powders P1 to P14 and P16 to P22, the hydrophobized acid reactive glass powder (a) itself was used. The powder P15 was prepared by mixing each of the components in the rate as shown in Table 5. Furthermore, the liquids L1 to L4 were prepared by mixing each of the components in the rates as shown in Table 6.

TABLE 4

Composition of powders P1 to P14 (% by mass)

|  |  | P1 | P2 | P3 | P4 | P5 | P6 | P7 | P8 | P9 | P10 | P11 | P12 | P13 | P14 |
|---|---|---|---|---|---|---|---|---|---|---|---|---|---|---|---|
| Component (a) | TG1 | 100 | — | — | — | — | — | — | — | — | — | — | — | — | — |
|  | TG2 | — | 100 | — | — | — | — | — | — | — | — | — | — | — | — |
|  | TG3 | — | — | 100 | — | — | — | — | — | — | — | — | — | — | — |
|  | TG4 | — | — | — | 100 | — | — | — | — | — | — | — | — | — | — |
|  | TG5 | — | — | — | — | 100 | — | — | — | — | — | — | — | — | — |

TABLE 4-continued

Composition of powders P1 to P14 (% by mass)

|  |  | P1 | P2 | P3 | P4 | P5 | P6 | P7 | P8 | P9 | P10 | P11 | P12 | P13 | P14 |
|---|---|---|---|---|---|---|---|---|---|---|---|---|---|---|---|
|  | TG6 | — | — | — | — | — | 100 | — | — | — | — | — | — | — | — |
|  | TG7 | — | — | — | — | — | — | 100 | — | — | — | — | — | — | — |
|  | TG8 | — | — | — | — | — | — | — | 100 | — | — | — | — | — | — |
|  | TG9 | — | — | — | — | — | — | — | — | 100 | — | — | — | — | — |
|  | TG10 | — | — | — | — | — | — | — | — | — | 100 | — | — | — | — |
|  | TG11 | — | — | — | — | — | — | — | — | — | — | 100 | — | — | — |
|  | TG12 | — | — | — | — | — | — | — | — | — | — | — | — | — | — |
|  | TG13 | — | — | — | — | — | — | — | — | — | — | — | — | — | — |
|  | TG14 | — | — | — | — | — | — | — | — | — | — | — | — | — | — |
|  | TG15 | — | — | — | — | — | — | — | — | — | — | — | — | — | — |
|  | TG16 | — | — | — | — | — | — | — | — | — | — | — | — | — | — |
|  | TG17 | — | — | — | — | — | — | — | — | — | — | — | — | — | — |
|  | TG18 | — | — | — | — | — | — | — | — | — | — | — | — | — | — |
| Component (b) | PCA1 | — | — | — | — | — | — | — | — | — | — | — | — | — | — |
| Others | G1 | — | — | — | — | — | — | — | — | — | — | — | 100 | — | — |
|  | G3 | — | — | — | — | — | — | — | — | — | — | — | — | 100 | — |
|  | G4 | — | — | — | — | — | — | — | — | — | — | — | — | — | 100 |
| Total |  | 100 | 100 | 100 | 100 | 100 | 100 | 100 | 100 | 100 | 100 | 100 | 100 | 100 | 100 |

TABLE 5

Composition of powders P15 to P22 (% by mass)

|  |  | P15 | P16 | P17 | P18 | P19 | P20 | P21 | P22 |
|---|---|---|---|---|---|---|---|---|---|
| Component (a) | TG1 | 95 | — | — | — | — | — | — | — |
|  | TG2 | — | — | — | — | — | — | — | — |
|  | TG3 | — | — | — | — | — | — | — | — |
|  | TG4 | — | — | — | — | — | — | — | — |
|  | TG5 | — | — | — | — | — | — | — | — |
|  | TG6 | — | — | — | — | — | — | — | — |
|  | TG7 | — | — | — | — | — | — | — | — |
|  | TG8 | — | — | — | — | — | — | — | — |
|  | TG9 | — | — | — | — | — | — | — | — |
|  | TG10 | — | — | — | — | — | — | — | — |
|  | TG11 | — | — | — | — | — | — | — | — |
|  | TG12 | — | 100 | — | — | — | — | — | — |
|  | TG13 | — | — | 100 | — | — | — | — | — |
|  | TG14 | — | — | — | 100 | — | — | — | — |
|  | TG15 | — | — | — | — | 100 | — | — | — |
|  | TG16 | — | — | — | — | — | 100 | — | — |
|  | TG17 | — | — | — | — | — | — | 100 | — |
|  | TG18 | — | — | — | — | — | — | — | 100 |
| Component (b) | PCA1 | 5 | — | — | — | — | — | — | — |
| Others | G1 | — | — | — | — | — | — | — | — |
|  | G3 | — | — | — | — | — | — | — | — |
|  | G4 | — | — | — | — | — | — | — | — |
| Total |  | 100 | 100 | 100 | 100 | 100 | 100 | 100 | 100 |

TABLE 6

Composition of liquids (% by mass)

|  |  | L1 | L2 | L3 | L4 |
|---|---|---|---|---|---|
| Component (b) | PCA1 | 45.0 | — | 60.0 | 30.0 |
|  | PCA2 | — | 40.0 | — | — |
| Component (c) | IEW | 48.5 | 53.9 | 38.0 | 60.0 |
| Others | TA | 6.5 | 6.1 | 2.0 | 10.0 |
| Total |  | 100.0 | 100.0 | 100.0 | 100.0 |

For the dental glass ionomer cement compositions (Examples 1 to 28, and Comparative Examples 1 to 5) in which the aforementioned powders and liquids were mixed by the combinations, powder to liquid ratios and mixing methods as shown in Examples and Comparative Examples of Tables 7 to 10, their mixing properties, compressive strengths, and fluoride-release properties were evaluated in accordance with the aforementioned methods. Tables 7 to 10 show their results.

TABLE 7

| Combination of Examples 1 to 10, Evaluation results |||||||
|---|---|---|---|---|---|---|
| | | Example 1 | Example 2 | Example 3 | Example 4 | Example 5 |
| Powder | | P1 | P1 | P4 | P5 | P6 |
| Liquid | | L1 | L1 | L1 | L1 | L1 |
| Powder to liquid ration[1)] | | 2.7/1.0 | 3.1/1.0 | 2.7/1.0 | 2.7/1.0 | 2.7/1.0 |
| purpose | | Filling material | Filling material | Filling material | Filling material | Filling material |
| Mixing method | | Mechanical mixing | Mechanical mixing | Mechanical mixing | Mechanical mixing | Mechanical mixing |
| Component (a) (% by mass) | TG1 | 73.0 | 75.6 | — | — | — |
| | TG2 | — | — | — | — | — |
| | TG3 | — | — | — | — | — |
| | TG4 | — | — | 73.0 | — | — |
| | TG5 | — | — | — | 73.0 | — |
| | TG6 | — | — | — | — | 73.0 |
| | TG7 | — | — | — | — | — |
| | TG8 | — | — | — | — | — |
| | TG10 | — | — | — | — | — |
| | TG11 | — | — | — | — | — |
| | TG12 | — | — | — | — | — |
| | TG13 | — | — | — | — | — |
| | TG14 | — | — | — | — | — |
| | TG15 | — | — | — | — | — |
| | TG16 | — | — | — | — | — |
| | TG17 | — | — | — | — | — |
| | TG18 | — | — | — | — | — |
| Component (b) (% by mass) | PCA1 | 12.2 | 11.0 | 12.2 | 12.2 | 12.2 |
| | PCA2 | — | — | — | — | — |
| Component (c) (% by mass) | IEW | 13.0 | 11.8 | 13.0 | 13.0 | 13.0 |
| Others (% by mass) | TA | 1.8 | 1.6 | 1.8 | 1.8 | 1.8 |
| Total (% by mass) | | 100.0 | 100.0 | 100.0 | 100.0 | 100.0 |
| Mixing property | | ◎ | ◎ | ◎ | ◎ | ◎ |
| Compressive strength(MPa) | | 234 | 245 | 225 | 217 | 232 |
| Evaluation | | ◎ | ◎ | ○ | Δ | ◎ |
| Fluoride-release property (ppm) | | 28 | 30 | 26 | 25 | 27 |
| Evaluation | | ◎ | ◎ | ◎ | ◎ | ◎ |
| Total Evaluation | | A | A | B | C | A |

| | | Example 6 | Example 7 | Example 8 | Example 9 | Example 10 |
|---|---|---|---|---|---|---|
| Powder | | P7 | P8 | P4 | P4 | P1 |
| Liquid | | L1 | L1 | L3 | L4 | L2 |
| Powder to liquid ration[1)] | | 2.7/1.0 | 2.7/1.0 | 4.0/1.0 | 4.2/1.0 | 2.7/1.0 |
| purpose | | Filling material | Filling material | Filling material | Filling material | Filling material |
| Mixing method | | Mechanical mixing | Mechanical mixing | Mechanical mixing | Mechanical mixing | Mechanical mixing |
| Component (a) (% by mass) | TG1 | — | — | — | — | 73.0 |
| | TG2 | — | — | — | — | — |
| | TG3 | — | — | — | — | — |
| | TG4 | — | — | 80.0 | 80.8 | — |
| | TG5 | — | — | — | — | — |
| | TG6 | — | — | — | — | — |
| | TG7 | 73.0 | — | — | — | — |
| | TG8 | — | 73.0 | — | — | — |
| | TG10 | — | — | — | — | — |
| | TG11 | — | — | — | — | — |
| | TG12 | — | — | — | — | — |
| | TG13 | — | — | — | — | — |
| | TG14 | — | — | — | — | — |
| | TG15 | — | — | — | — | — |
| | TG16 | — | — | — | — | — |
| | TG17 | — | — | — | — | — |
| | TG18 | — | — | — | — | — |

TABLE 7-continued

Combination of Examples 1 to 10, Evaluation results

| | | | | | | |
|---|---|---|---|---|---|---|
| Component (b) (% by mass) | PCA1 | 12.2 | 12.2 | 12.0 | 5.8 | — |
| | PCA2 | — | — | — | — | 10.8 |
| Component (c) (% by mass) | IEW | 13.0 | 13.0 | 7.6 | 11.5 | 14.6 |
| Others (% by mass) | TA | 1.8 | 1.8 | 0.4 | 1.9 | 1.6 |
| Total (% by mass) | | 100.0 | 100.0 | 100.0 | 100.0 | 100.0 |
| Mixing property | | ◉ | ◉ | Δ | Δ | ◉ |
| Compressive strength(MPa) | | 236 | 235 | 228 | 218 | 238 |
| Evaluation | | ◉ | ◉ | ○ | Δ | ◉ |
| Fluoride-release property (ppm) | | 28 | 26 | 28 | 27 | 26 |
| Evaluation | | ◉ | ◉ | ◉ | ◉ | ◉ |
| Total Evaluation | | A | A | D | E | A |

[1] Powder to liquid ratio: Mass ratio of powder to liquid (powder mass/liquid mass) upon mixing.

TABLE 8

Combination of Examples 11 to 17, Evaluation results

| | | Example 11 | Example 12 | Example 13 | Example 14 | Example 15 | Example 16 | Example 17 |
|---|---|---|---|---|---|---|---|---|
| Powder | | P11 | P15 | P4 | P4 | P17 | P18 | P16 |
| Liquid | | L1 | L1 | L3 | L4 | L1 | L1 | L1 |
| Powder to liquid ratio[1] | | 2.7/1.0 | 2.7/1.0 | 4.1/1.0 | 4.3/1.0 | 2.7/1.0 | 2.7/1.0 | 2.7/1.0 |
| Purpose | | Filling material | Filling material | Filling material | Filling material | Filling material | Filling material | Filling material |
| Mixing method | | Mechanical mixing | Mechanical mixing | Mechanical mixing | Mechanical mixing | Mechanical mixing | Mechanical mixing | Mechanical mixing |
| Component (a) (% by mass) | TG1 | — | 69.2 | — | — | — | — | — |
| | TG2 | — | — | — | — | — | — | — |
| | TG3 | — | — | — | — | — | — | — |
| | TG4 | — | — | 80.4 | 81.1 | — | — | — |
| | TG5 | — | — | — | — | — | — | — |
| | TG6 | — | — | — | — | — | — | — |
| | TG7 | — | — | — | — | — | — | — |
| | TG8 | — | — | — | — | — | — | — |
| | TG10 | — | — | — | — | — | — | — |
| | TG11 | 73.0 | — | — | — | — | — | — |
| | TG12 | — | — | — | — | — | — | 73.0 |
| | TG13 | — | — | — | — | 73.0 | — | — |
| | TG14 | — | — | — | — | — | 73.0 | — |
| | TG15 | — | — | — | — | — | — | — |
| | TG16 | — | — | — | — | — | — | — |
| | TG17 | — | — | — | — | — | — | — |
| | TG18 | — | — | — | — | — | — | — |
| Component (b) (% by mass) | PCA1 | 12.2 | 15.9 | 11.7 | 5.7 | 12.2 | 12.2 | 12.2 |
| | PCA2 | — | — | — | — | — | — | — |
| Component (c) (% by mass) | IEW | 13.0 | 13.1 | 7.5 | 11.3 | 13.0 | 13.0 | 13.0 |
| Other (% by mass) | TA | 1.8 | 1.8 | 0.4 | 1.9 | 1.8 | 1.8 | 1.8 |
| Total (% by mass) | | 100.0 | 100.0 | 100.0 | 100.0 | 100.0 | 100.0 | 100.0 |
| Mixing property | | ◉ | ◉ | Δ | Δ | ◉ | ◉ | ◉ |
| Compressive strength (MPa) | | 221 | 235 | 213 | 216 | 233 | 231 | 201 |
| Evaluation | | ○ | ◉ | Δ | Δ | ◉ | ◉ | ▲ |
| Fluoride-release property (ppm) | | 22 | 27 | 28 | 27 | 27 | 26 | 18 |
| Evaluation | | ○ | ◉ | ◉ | ◉ | ◉ | ◉ | Δ |
| Total Evaluation | | C | A | E | E | A | A | F |

[1] Powder to liquid ratio: Mass ratio of powder to liquid (powder mass/liquid mass) upon mixing.

TABLE 9

Combination of Examples 18 to 28, Evaluation results

| | | Example 18 | Example 19 | Example 20 | Example 21 | Example 22 | Example 23 |
|---|---|---|---|---|---|---|---|
| Powder | | P19 | P20 | P2 | P3 | P3 | P3 |
| Liquid | | L1 | L1 | L1 | L1 | L3 | L4 |
| Powder to liquid ratio[1] | | 1.8/1.0 | 1.8/1.0 | 1.6/1.0 | 1.6/1.0 | 1.2/1.0 | 1.2/1.0 |
| Purpose | | Luting material | Luting material | Luting material | Luting material | Luting material | Luting material |
| Mixing method | | Mechanical mixing | Mechanical mixing | Mechanical mixing | Mechanical mixing | Mechanical mixing | Mechanical mixing |
| Component (a) (% by mass) | TG1 | — | — | — | — | — | — |
| | TG2 | — | — | 61.5 | — | — | — |
| | TG3 | — | — | — | 61.5 | 54.5 | 54.5 |
| | TG4 | — | — | — | — | — | — |
| | TG5 | — | — | — | — | — | — |
| | TG6 | — | — | — | — | — | — |
| | TG7 | — | — | — | — | — | — |
| | TG8 | — | — | — | — | — | — |
| | TG10 | — | — | — | — | — | — |
| | TG11 | — | — | — | — | — | — |
| | TG12 | — | — | — | — | — | — |
| | TG13 | — | — | — | — | — | — |
| | TG14 | — | — | — | — | — | — |
| | TG15 | 64.3 | — | — | — | — | — |
| | TG16 | — | 64.3 | — | — | — | — |
| | TG17 | — | — | — | — | — | — |
| | TG18 | — | — | — | — | — | — |
| Component (b) (% by mass) | PCA1 | 16.1 | 16.1 | 17.3 | 17.3 | 27.3 | 13.6 |
| | PCA2 | — | — | — | — | — | — |
| Component (c) (% by mass) | IEW | 17.3 | 17.3 | 18.7 | 18.7 | 17.3 | 27.3 |
| Others (% by mass) | TA | 2.3 | 2.3 | 2.5 | 2.5 | 0.9 | 4.6 |
| Total (% by mass) | | 100.0 | 100.0 | 100.0 | 100.0 | 100.0 | 100.0 |
| Mixing property | | ◎ | ◎ | ◎ | ◎ | ◎ | ◎ |
| Compressive strength (MPa) | | 174 | 176 | 146 | 156 | 151 | 153 |
| Evaluation | | ◎ | ◎ | ▲ | Δ | Δ | Δ |
| Fluoride-release property (ppm) | | 33 | 28 | 16 | 22 | 21 | 21 |
| Evaluation | | ◎ | ◎ | Δ | ○ | ○ | ○ |
| Total Evaluation | | A | A | F | D | D | D |

| | | Example 24 | Example 25 | Example 26 | Example 27 | Example 28 |
|---|---|---|---|---|---|---|
| Powder | | P10 | P3 | P3 | P21 | P22 |
| Liquid | | L1 | L3 | L4 | L1 | L1 |
| Powder to liquid ratio[1] | | 1.6/1.0 | 1.1/1.0 | 1.1/1.0 | 1.8/1.0 | 1.8/1.0 |
| Purpose | | Luting material | Luting material | Luting material | Luting material | Luting material |
| Mixing method | | Mechanical mixing | Mechanical mixing | Mechanical mixing | Mechanical mixing | Mechanical mixing |
| Component (a) (% by mass) | TG1 | — | — | — | — | — |
| | TG2 | — | — | — | — | — |
| | TG3 | — | 52.4 | 52.4 | — | — |
| | TG4 | — | — | — | — | — |
| | TG5 | — | — | — | — | — |
| | TG6 | — | — | — | — | — |
| | TG7 | — | — | — | — | — |
| | TG8 | — | — | — | — | — |
| | TG10 | 61.5 | — | — | — | — |
| | TG11 | — | — | — | — | — |
| | TG12 | — | — | — | — | — |
| | TG13 | — | — | — | — | — |
| | TG14 | — | — | — | — | — |
| | TG15 | — | — | — | — | — |
| | TG16 | — | — | — | — | — |
| | TG17 | — | — | — | 64.3 | — |
| | TG18 | — | — | — | — | 64.3 |

TABLE 9-continued

Combination of Examples 18 to 28, Evaluation results

| | | | | | | |
|---|---|---|---|---|---|---|
| Component (b) (% by mass) | PCA1 | 17.3 | 28.6 | 14.2 | 16.1 | 16.1 |
| | PCA2 | — | — | — | — | — |
| Component (c) (% by mass) | IEW | 18.7 | 18.0 | 28.6 | 17.3 | 17.3 |
| Others (% by mass) | TA | 2.5 | 1.0 | 4.8 | 2.3 | 2.3 |
| Total (% by mass) | | 100.0 | 100.0 | 100.0 | 100.0 | 100.0 |
| Mixing property | | Δ | ⊚ | ⊚ | ⊚ | ⊚ |
| Compressive strength (MPa) | | 155 | 142 | 141 | 168 | 166 |
| Evaluation | | Δ | ▲ | ▲ | ○ | ○ |
| Fluoride-release property (ppm) | | 30 | 16 | 15 | 27 | 25 |
| Evaluation | | ⊚ | Δ | Δ | ⊚ | ⊚ |
| Total Evaluation | | E | F | F | B | B |

[1]Powder to liquid ratio: Mass ratio of powder to liquid (powder mass/liquid mass) upon mixing.

TABLE 10

Combination of Comparative Examples 1 to 5, Evaluation results

| | | Comparative Example 1 | Comparative Example 2 | Comparative Example 3 | Comparative Example 4 | Comparative Example 5 |
|---|---|---|---|---|---|---|
| Powder | | P12 | P1 | P13 | P14 | P9 |
| Liquid | | L1 | L1 | L1 | L1 | L1 |
| Powder to liquid ration[1] | | 2.7/1.0 | 2.7/1.0 | 1.8/1.0 | 2.7/1.0 | 2.7/1.0 |
| Purpose | | Filling material | Filling material | Luting material | Filling material | Filling material |
| Mixing method | | Mechanical mixing | Hand mixing | Mechanical mixing | Mechanical mixing | Mechanical mixing |
| Component (a) (% by mass) | TG1 | — | 73.0 | — | — | — |
| | TG9 | — | — | — | — | 73.0 |
| | G1 | 73.0 | — | — | — | — |
| | G3 | — | — | 64.3 | — | — |
| | G4 | — | — | — | 73.0 | — |
| Component (b) (% by mass) | PCA1 | 12.2 | 12.2 | 16.1 | 12.2 | 12.2 |
| Component (c) (% by mass) | IEW | 13.0 | 13.0 | 17.3 | 13.0 | 13.0 |
| Others (% by mass) | TA | 1.8 | 1.8 | 2.3 | 1.8 | 1.8 |
| Total (% by mass) | | 100.0 | 100.0 | 100.0 | 100.0 | 100.0 |
| Mixing property | | × | ×[2] | × | × | × |
| Compressive strength (MPa) | | 188 | 19  8 | 121 | 182 | 187 |
| Evaluation | | × | × | × | × | × |
| Fluoride-release property (ppm) | | 28 | 27 | 31 | 25 | 28 |
| Evaluation | | ⊚ | ⊚ | ⊚ | ⊚ | ⊚ |
| Total Evaluation | | I | I | I | I | I |

[1]Powder to liquid ratio: Mass ratio of powder to liquid (powder material mass/liquid mass) upon mixing
[2]Powder and liquid were hard to be adapted to each other, mixing efficiency was poor, and a lot of powder remains in the cement mixture.
Therefore, the dental glass ionomer cement composition was not suitable for hand mixing Example 1

The dental glass ionomer cement composition of Example 1 exhibited a good mixing property in the mechanical mixing, and had a high compressive strength. Furthermore, the cement composition exhibited an excellent fluoride-release property, and had properties desirable as dental glass ionomer cements.

Examples 2 to 28

Summary of compositions of Examples 2 to 28 were as follows:

Example 2: Composition in which the Powder to Liquid Ratio was Raised from that of Example 1

Examples 3 to 4, 11, 15 to 21, 24, 27, and 28: Compositions in which the particle size of acid reactive glass powder, the treating amounts of hydrophobizing surface treatment agent, and powder to liquid ratios were modified from those of Example 1.

Examples 5 to 7: Compositions in which the Kind of Hydrophobizing Surface Treatment Agent was Modified from that of Example 1

Examples 8 to 9, 13 to 14, 22 to 23, 25, and 26: Compositions which used the liquids in which the concentrations of their polyalkene acid (b) differ from each other Example 10: Composition in which the Kind of the Polyalkene Acid (b) was Modified from that of Example 1

Example 12: Composition in which the Polyalkene Acid (b) was Blended to the Powder from Example 1

As results of evaluating Examples 2 to 28, all examples exhibited a good mixing property in the mechanical mixing, and they had high compressive strengths. Furthermore, they exhibited an excellent fluoride-release property, and had properties desirable as dental glass ionomer cements.

Comparative Example 1

Comparative Example 1 is for a composition in which an acid reactive glass powder, which has the same particle size as in Example 1 and is not surface treated, was blended, instead of the hydrophobized acid reactive glass powder (a) of Example 1 [50% particle size (D50): 4.7 μm and treating amount: 0.30 parts by mass]. As a result of evaluating Comparative Example 1, in the mechanical mixing, the mixing property was poor, and the compressive strength was low.

Comparative Example 2

Comparative Example 2 is for a composition in which a hand mixing for Example 1 was carried out. As a result of evaluating Comparative Example 2, since its powder and liquid are difficult to be adopted, and the mixing efficiency was poor, it was not suitable for the hand mixing. Further, the compressive strength was low.

Comparative Example 3

Comparative Example 3 is for a composition in which an acid reactive glass powder, which has the same particle size as in Example 18 and is not surface treated, was blended, instead of the hydrophobized acid reactive glass powder (a) of Example 18 [50% particle size (D50): 0.5 μm and treating amount: 1.00 parts by mass]. As a result of evaluating Comparative Example 3, in the mechanical mixing, the mixing property was poor, and the compressive strength was low.

Comparative Example 4

Comparative Example 4 is for a composition in which an acid reactive glass powder, which has the same particle size as in Example 3 and is not surface treated, was blended, instead of the hydrophobized acid reactive glass powder (a) of Example 3 [50% particle size (D50): 15.0 μm and treating amount: 0.05 parts by mass]. As a result of evaluating Comparative Example 4, in the mechanical mixing, the mixing property was poor, and the compressive strength was low.

Comparative Example 5

Comparative Example 5 is for a composition in which an acid reactive glass powder, which is hydrophilically surface treated by using γ-aminopropyltrimethoxysilane as a surface treatment agent, was blended, instead of the hydrophobized acid reactive glass powder (a)(hydrophobizing surface treatment agent: γ-methacryloyloxypropyltrimethoxysilane) of Example 1. As a result of evaluating Comparative Example 5, in the mechanical mixing, the mixing property was poor, and the compressive strength was low.

The invention claimed is:

1. A dental glass ionomer cement composition mechanically mixed by using a capsule mixer, the dental glass ionomer cement composition comprising:
   (a) a hydrophobized acid reactive glass powder,
   (b) a polyalkene acid, and
   (c) water,
   wherein the dental glass ionomer cement composition does not comprise a compound having a polymerizable group selected from the group consisting of a polymerizable monomer, an oligomer having polymerizable group(s) and a polymer having polymerizable group(s).

2. The dental glass ionomer cement composition according to claim 1, wherein the (a) hydrophobic acid-reactive glass powder is an acid-reactive glass powder having 0.5-15 μm particle size in 50% of volume-based cumulative particle distribution (D50) and hydrophobized with a hydrophobic surface treatment agent.

3. The dental glass ionomer cement composition according to claim 2, wherein the hydrophobizing surface treatment agent is at least one hydrophobizing surface treatment agent selected from the group consisting of:
   a silane coupling agent represented by formula (1):

$$R_n SiA_{4-n} \quad (1)$$

wherein R is an optionally substituted hydrocarbon group with a carbon number of 1 to 20, A is an alkoxy group with a carbon number of 1 to 4, an alkoxyalkoxy group with a carbon number of 2 to 10, an acyloxy group with a carbon number of 1 to 6, an alkenyloxy group with a carbon number of 2 to 6, a halogen atom, an isocyanate group, a hydroxy group, or a hydrogen atom, and n is an integer of 1 to 3, provided that a plurality of R and A may be the same or differ from each other, and
   an organosilazane represented by formula (2):

$$R^1 R^2 R^3-Si-NH-Si-R^4 R^5 R^6 \quad (2)$$

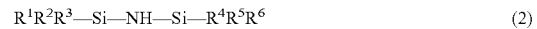

wherein $R^1$, $R^2$, and $R^3$ are independently a hydrogen atom or an optionally substituted hydrocarbon group with a carbon number of 1 to 6, wherein at least one of $R^1$, $R^2$, and $R^3$ is an optionally substituted hydrocarbon group with a carbon number of 1 to 6, and $R^4$, $R^5$, and $R^6$ are independently a hydrogen or an optionally substituted hydrocarbon group with a carbon number of 1 to 6, wherein at least one of $R^4$, $R^5$, and $R^6$ is an optionally substituted hydrocarbon group with a carbon number of 1 to 6.

4. The dental glass ionomer cement composition according to claim 1, wherein the composition comprises, based on the total dental glass ionomer cement composition,
   (a) 54.5 to 80.0% by mass of the hydrophobized acid reactive glass powder,
   (b) 5.8 to 27.3% by mass of the polyalkene acid, and
   (c) 7.6 to 27.3% by mass of the water.

5. The dental glass ionomer cement composition according to claim 1, wherein the hydrophobized acid reactive glass powder (a) is hydrophobization-treated with 0.05 to 3.0 parts by mass of the hydrophobizing surface treatment agent based on 100 parts by mass of an acid reactive glass powder.

6. The dental glass ionomer cement composition according to claim 1, wherein the dental glass ionomer cement composition is constituted from a powder and a liquid, wherein the powder and the liquid are separately packaged in a dental capsule, and wherein the hydrophobized acid reactive glass powder (a) is contained in the powder, the water (c) is contained in the liquid, and the polyalkene acid (b) is contained in at least one of the powder and the liquid.

* * * * *